United States Patent [19]

Jones

[11] 4,256,333
[45] Mar. 17, 1981

[54] SOLVENT-BONDED JOINT

[75] Inventor: Eugene C. Jones, Laguna Niguel, Calif.

[73] Assignee: American Hospital Supply Corporation, Evanston, Ill.

[21] Appl. No.: 924,442

[22] Filed: Jul. 13, 1978

Related U.S. Application Data

[62] Division of Ser. No. 776,430, Mar. 10, 1977, Pat. No. 4,137,117.

[51] Int. Cl.³ ............................................. F16L 13/10
[52] U.S. Cl. ............................................ 285/22; 285/3; 285/93; 285/331; 285/423; 285/DIG. 16
[58] Field of Search .................. 285/21, 22, DIG. 16, 285/3, 4, 331, 334.4, 423, 287, 294, 297, 93; 156/294, 305; 138/89

[56] References Cited

U.S. PATENT DOCUMENTS

| | | | |
|---|---|---|---|
| 693,830 | 2/1902 | Burke | 285/297 |
| 2,498,831 | 2/1950 | Veitch | 285/DIG. 16 |
| 2,741,402 | 4/1956 | Sayre | 285/21 X |
| 3,224,795 | 12/1965 | Conley | 285/331 X |
| 3,264,013 | 8/1966 | Richardson et al. | 285/423 X |
| 3,473,833 | 10/1969 | Bremer | 285/331 X |
| 3,654,965 | 4/1972 | Gramain | 138/89 |
| 3,726,320 | 4/1973 | Lachenmayer | 285/331 X |
| 3,920,787 | 11/1975 | McDowell | 285/21 X |

FOREIGN PATENT DOCUMENTS

| | | | |
|---|---|---|---|
| 1530648 | 5/1968 | France | 285/22 |
| 986227 | 3/1965 | United Kingdom | 285/260 |

*Primary Examiner*—Dave W. Arola
*Attorney, Agent, or Firm*—Tilton, Fallon, Lungmus & Chestnut

[57] ABSTRACT

A solvent-bonded joint between plastic members, particularly useful where such members are intended to convey flowable materials such as sterile medical solutions. The joint includes a pair of members joined at a zone of interference, a tapered crevice between the members, a solvent bond in the tapered crevice, and a series of spacers extending along the entrance to the crevice.

4 Claims, 7 Drawing Figures

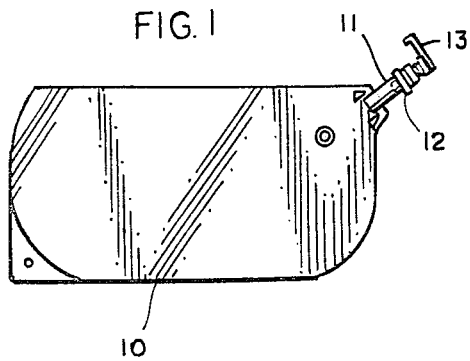
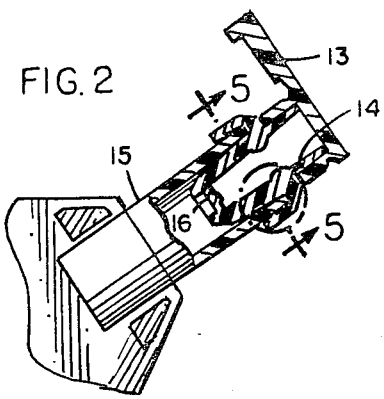
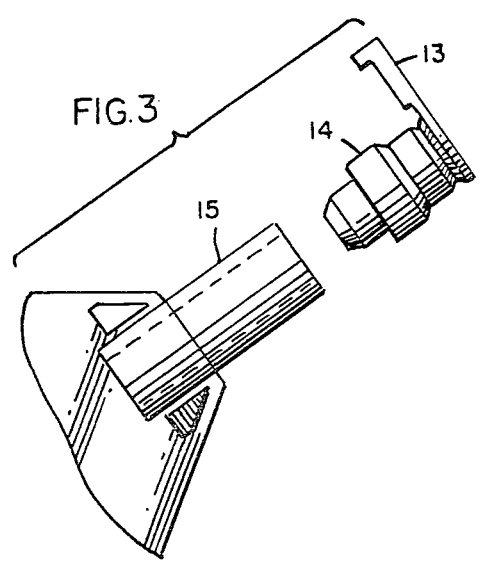
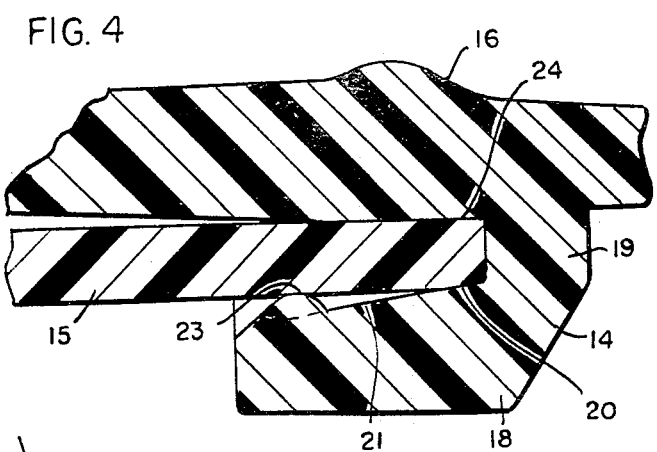
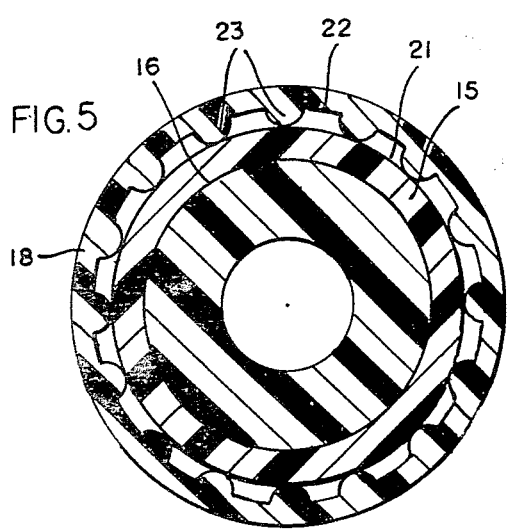
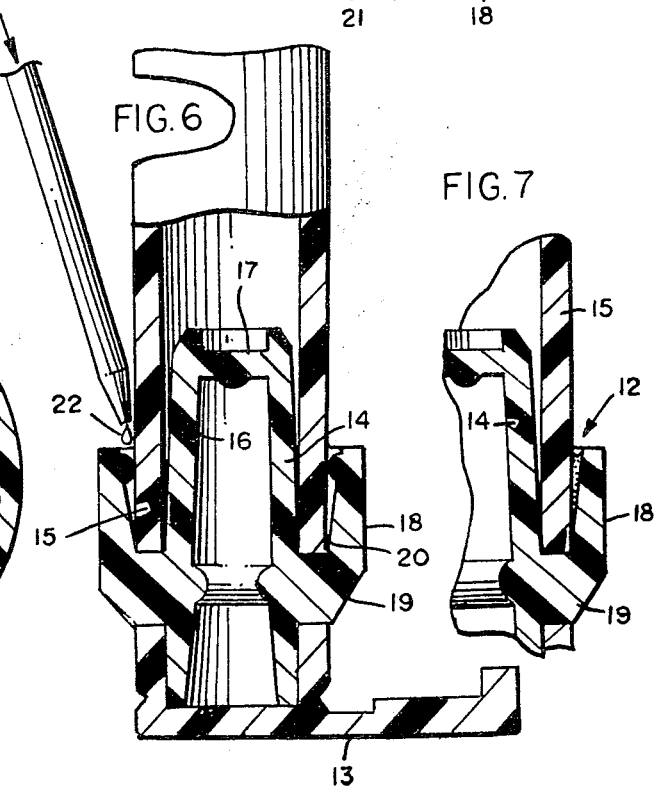
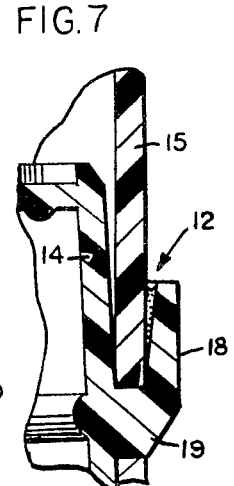

SOLVENT-BONDED JOINT

RELATED APPLICATION

This application is a division of my co-pending application Ser. No. 776,430, filed Mar. 10, 1977, entitled Solvent-Bonded Joint and Method of Making the Same and now U.S. Pat. No. 4,137,117 issued June 30, 1979.

BACKGROUND

Various methods have been used in the past for permanently joining plastic parts in fluid-tight sealing relation, including heat sealing and solvent-bonding techniques. Heat sealing, although widely used, ordinarily requires elaborate supports and operating mechanisms to achieved reliability and production volume in the assembly of relatively small plastic parts such as, for example, filter housing, couplings, port assemblies, and other elements and assemblies commonly used in medical equipment.

Solvent sealing, which ordinarily involves coating one of the parts with solvent before the two parts are fitted together, is suitable for some operations but has severe limitations for volume production. Parts once coated must be immediately assembled; it is not feasible, for example, to coat successively a multiplicity of parts and then assemble them in a batch-type operation. Also, in those cases where one of the parts contains (or communicates with) a liquid, the usual solvent coating and fitting operations are not only awkward and unwieldly, but present risks of liquid interfering with proper solvent bonding and, even more important, of small amounts of solvent invading the liquid-containing compartment. It is apparent that any contact between the liquid or solvent is undesirable and, especially if it might result in contamination of the liquid (such as parenteral fluid), must be strictly avoided.

Patents indicating the state of the art are as follows: 2,302,244, 3,539,205, 3,700,531, 3,208,787, 3,473,833, 3,765,983, 2,983,639, 2,686,091, 3,830,173, 4,004,586, 3,768,476, 2,584,095, 3,278,357, 3,728,184, and 3,795,558.

SUMMARY

The solvent joint of this invention involves a pair of plastic parts or members frictionally engageable in a liquid-tight zone of interference, a tapered crevice between those members leading to the zone of interference with the zone of interference serving as a barrier against flow in either direction through the apex of the tapered crevice, and a permanent solvent bond between the members in at least the base of the tapered crevice. One or both of the plastic members is formed of resilient or flexible plastic material and, in the embodiment disclosed, the members are tubular with one of the members receiving the other in telescoping or overlapping relationship. The receiving member has an outer skirt which, together with the main portion of the receiving member, defines an annular channel or recess for receiving the end portion of the other telescoping member.

A series of uniformly- and circumferentially-spaced nubs or projections, formed integrally with at least one of the members, extends about the mouth of the crevice at the time of solvent introduction and serves to maintain the parts in concentric relation, with the mouth of the crevice at uniform width, throughout solvent sealing, thereby insuring the formation of a circumferentially-uniform solvent bond between the parts. The nubs may also contribute in retaining solvent immediately following its introduction and in providing a visual indication when the preferred amount of solvent has been introduced. When solvent has been added to the optimum level or extent, evaporation of such solvent is accompanied by concurrent dissolving of the nubs so that upon completion of the solvent bonding step the nubs are substantially if not entirely dissolved and the plastic thereof is reformed as part of the joint.

Other objects of the invention can be appreciated from the details of construction and operation set forth in the accompanying specification, claims, and drawings.

DRAWINGS

FIG. 1 is a front elevational view of a bag adapted for use in the administration of medical liquid, the bag utilizing the solvent-bonded joint of this invention.

FIG. 2 is a longitudinal sectional view showing the assembled parts just prior to solvent introduction and fusion.

FIG. 3 is a side elevational view showing the parts in exploded condition.

FIG. 4 is a greatly enlarged longitudinal sectional view of a portion indicated by a circle in FIG. 4.

FIG. 5 is an enlarged transverse cross sectional view taken along line 5—5 of FIG. 2.

FIG. 6 is an enlarged longitudinal sectional view showing the joint of the present invention during introduction of a solvent to form the solvent bond.

FIG. 7 is a fragmentary sectional view similar to FIG. 6 but showing the parts following solvent fusion.

DESCRIPTION

In the illustration given, and with reference first to FIG. 1, the numeral 10 generally designates a parenteral fluid administration bag having an outlet port assembly 11. The port assembly includes a solvent joint 12 (FIG. 7) formed in accordance with this invention. The solvent joint is particularly well suited for use in such medical liquid administration equipment for operatively connecting the components together even where one of the components (such as the bag of this illustration) contains such liquid at the time the solvent joint is formed.

The outlet portion assembly 11 includes a tear cap 13, a port closure 14, and an outlet tube or neck 15. The tube has one end attached to a corner of the bag 10 and communicates with the interior of that bag. Port closure 14 includes a tubular insert portion 16 which is received within the end of neck or tube 15 and which terminates in a diaphragm 17. The port closure also has a concentric outer skirt portion 18 which extends about the insert portion and is joined thereto by integral connecting portion 19.

The solvent joint 12 is formed between a pair of plastic members or parts which, in the illustration given, constitute the outlet tube or neck 15 and the outer portion or skirt 18 of port closure 14. It is to be understood, however, that the joint is shown as being operatively associated with an outlet port assembly primarily for purposes of illustrating one of the many advantageous applications of this invention. Accordingly, the solvent joint in the following description is equally well suited for joining plastic members of many different configurations within the contemplation of the present invention.

Referring to FIGS. 4 and 5, in which the parts are shown just prior to solvent introduction and fusion, members 15 and 18 are in fluid-tight frictional contact along an annular zone of interference 20. That zone of interference takes the form of direct sealing contact between the inner surface of skirt member 18 near the base thereof and the outer surface of tube member 15 adjacent its free end. A tapered crevice 21 extends from the free end of skirt member 18 to the zone of interference 20.

In the embodiment shown, member 18 is provided with a plurality of uniformly- and circumferentially-spaced enlargements or nubs 23 which bear against the outer surface of member 15 and which extend in a series substantially parallel with, but spaced from, the zone of interference 20. FIG. 4 reveals that the nubs or projections are disposed near the free end of skirt portion 18, that is, adjacent the mouth or entrance to the crevice and at a substantial axial distance from interference zone 20.

A second zone of interference 24 is located between the inner surface of port tube 15 (adjacent the end of that tube) and the outer surface of the base of insert 16. Therefore, insertion of the port tube 15 into the annular recess of the port closure 14 results in the formation of two fluid-tight sealing zones 20 and 24 with the enlargements or projections 23 of member 18 bearing forceably against the outer surface of member 15. The projections control the configuration of the tapered crevice 21, maintaining its dimensions substantially uniform throughout the entire circumference of the assembly and insuring that solvent introduced after the parts have been so pre-assembled will be distributed uniformly by a capillary action regardless of the circumferential location of solvent introduction.

It is believed apparent that the invention is of particular important where the cooperating members 15 and 18, or at least the latter of these members, are formed of flexible plastic material. Any flexible plastic material capable of being solvent bonded may be used. Examples are plasticized polyvinyl chloride and styrene butadiene; however, other solvent-bondable plastic materials having similar properties are well known and may be used.

The circumscribing skirt portion 18, which may be regarded as an overlapping or receiving member, has an inner surface which forms an angle of about 1 to 20 degrees, and preferably 2 to 6 degrees, with respect to the outer surface of member 15. Stated differently, in the preferred form of the invention the taper of crevice 21 is approximately 2 to 6 degrees. Such a relationship insures that solvent will wick into the crevice to the zone of interference 20 and will remain in the crevice even if the parts are inverted immediately following introduction of the solvent.

The method of joining the parts is as follows: the parts are first fitted together in frictional engagement as shown in FIGS. 2, 4, and 5. Precise relative positioning of the parts is easily achieved because no solvent is yet present and fusion has therefore not commenced. When the parts are properly interfitted, zone of interference 24 is formed and serves primarily as a liquid-tight barrier to block the flow of liquid (or other flowable material) from bag 10 to the tapered crevice 21 where it might otherwise wet the surfaces of that crevice and prevent the formation of an effective solvent bond.

The solvent bond 12 is formed by introducing solvent 22 into the mouth of crevice as indicated in FIG. 6. The liquid solvent spreads uniformly about member 15 within the crevice, exposing the opposing surfaces of the parts to uniform solvent action. While the amount of solvent might be varied according to preference, in the best mode presently known for practicing the invention a sufficient volume of solvent is added to surround the nubs or projections 23. Under such circumstances, the nubs serve as a gauge to indicate whether a sufficient solvent volume has been introduced. If the solvent bridges the space between adjacent nubs, then the volume of added solvent is at or near its optimum level.

Following addition of liquid solvent 22, the solvent beings to evaporate and also commences to dissolve the strata of plastic material in direct contact therewith. The final solvent-formed bond 12 results when evaporation is completed. At that time the parts assume the relationship somewhat schematically depicted in FIG. 7. It is to be understood that the material illustrated in the crevice and designated by a stippled shading, is resolidified plastic from members 14 and 15. Hence, the joint is a fusion joint and in actual practice the material in the previously-existing crevice is visually indistinguishable from the plastic members themselves. Furthermore, where the joint is formed by adding solvent to a level at or above projections 23, such projections no longer exist in their original form, at least to any appreciable extent, in the final joint. After functioning as spacers to insure uniform distribution of solvent within the crevice, such projections themselves dissolve, at least partly because of their relatively great surface area, and become part of the resolidified mass of material which fuses the parts together.

As the solvent is evaporating, interference zone 20 performs the function of blocking the escape of solvent through the apex of the crevice. Therefore, the two zones of interference, zones 20 and 24, together prevent contact between the liquid (or other flowable material) within the bag and the solvent introduced to form the permanent joint, eliminating the risk of contaminating the contents of the bag by solvent, and also reduce the danger that the flowable contents of the bag might impair the formation of an effective solvent bond. The result, following introduction of the solvent and evaporation thereafter, is a permanent solvent bond 12 which provides a contamination-proof and leak-proof joint between the parts.

The solvent 22 may be formulated from any of a variety of well-known plastic solvents such as, for example, cyclohexanone or tetrahydrofuran. As used herein, the term "solvent" means any liquid bonding agent which has some capability of dissolving or softening the plastic material or materials from which the parts are formed, even though such agent may also contain fillers or other ingredients which have no such properties. Thus, a bodied solvent, or a cement having a liquid medium which is also a solvent for the plastic materials, is regarded as a solvent within the meaning of this application.

While in the foregoing specification a detailed description of the invention has been set forth for the purpose of illustration, variation of the details herein given may be made by those skilled in the art without departing from the spirit and scope of the invention.

I claim:

1. In combination, a pair of flexible plastic tubular members frictionally joined directly together along a fluid-tight zone of interference with an elongated gradually-tapered crevice between said members extending towards said zone, said members including an outer member and an inner member, said outer member having an end portion telescopingly receiving an end portion of said inner member, said zone of interference being disposed adjacent the end portion of said inner member, said outer tubular member having an integral tubular insert portion disposed within said inner member, said insert portion frictionally engaging the inner surface of said inner member to form a second fluid-tight zone of interference and bracing said inner member against inward flexure in response to inward forces exerted upon said inner member by said outer member at said first zone of interference, said tapered crevice between said members being adapted to receive liquid solvent for forming a solvent bond, at least one of said flexible plastic members being provided with a plurality of circumferentially-spaced integral nubs disposed within said crevice adjacent the mouth thereof and engaging the other of said members for maintaining a generally uniform annular spacing between said members at the mouth of said crevice.

2. The combination of claim 1 in which said insert portion includes an imperforate transverse wall.

3. The combination of claim 1 in which said nubs are provided by said outer flexible plastic member.

4. The combination of claim 1 in which a solvent bond fuses together the plastic material of said members within said crevice.

* * * * *